United States Patent
George et al.

(10) Patent No.: US 11,938,103 B2
(45) Date of Patent: Mar. 26, 2024

(54) POTENTIATION OF HELMINTH TREATMENT

(71) Applicant: Elanco Tiergesundheit AG, Greenfield, IN (US)

(72) Inventors: Sarah George, Oakdale (AU); Peter Rolfe, Gunning (AU); Chouaib Tahtaoui, Rixheim (FR)

(73) Assignee: Elanco Tiergesundheit AG, Greenfield, IN (US)

( * ) Notice: Subject to any disclaimer, the term of this patent is extended or adjusted under 35 U.S.C. 154(b) by 293 days.

(21) Appl. No.: 17/281,914

(22) PCT Filed: Sep. 30, 2019

(86) PCT No.: PCT/US2019/053750
§ 371 (c)(1),
(2) Date: Mar. 31, 2021

(87) PCT Pub. No.: WO2020/072343
PCT Pub. Date: Apr. 9, 2020

(65) Prior Publication Data
US 2022/0008366 A1     Jan. 13, 2022

Related U.S. Application Data

(60) Provisional application No. 62/741,120, filed on Oct. 4, 2018.

(51) Int. Cl.
*A61K 31/167*     (2006.01)
*A61K 31/63*     (2006.01)
*A61P 33/10*     (2006.01)

(52) U.S. Cl.
CPC ............ *A61K 31/167* (2013.01); *A61K 31/63* (2013.01); *A61P 33/10* (2018.01)

(58) Field of Classification Search
CPC ...... A61K 31/167; A61K 31/63; A61K 31/18; A61D 7/00; A61P 33/10; A61P 33/00; A61P 43/00
See application file for complete search history.

(56) References Cited

FOREIGN PATENT DOCUMENTS

WO     WO-9428887 A1 * 12/1994 ........... A61K 31/275

OTHER PUBLICATIONS

McKellar Br. Vet. J. 1991, 147, p. 306-321 (Year: 1991).*
Fairweather et al. The Veterinary Journal, 1999, 158, 81-112. (Year: 1999).*
Valladares et al., "Efficacy of an anthelmintic combination in sheep infected with Fasciola hepatica resistant to albendazole and clorsulon", Experimental Parasitology, vol. 136, Jan. 2014, pp. 59-62.

* cited by examiner

*Primary Examiner* — Kara R McMillian
(74) *Attorney, Agent, or Firm* — McBee Moore & Vanik IP, LLC

(57) ABSTRACT

The present invention provides a method of treating liver fluke infections in a mammal in need of such treatment comprising administering an effective amount of diamphenethide in combination with an effective amount of clorsulon.

8 Claims, No Drawings

POTENTIATION OF HELMINTH TREATMENT

CROSS-REFERENCE TO RELATED APPLICATIONS

This application is a national filing of PCT/US2019/053750 filed Sep. 30, 2019, and published in English as WO/2020/072343, which claims the benefit of priority to U.S. Provisional patent application Ser. No. 62/741,120, filed Oct. 4, 2018, each of which is incorporated herein by reference in its entirety.

BACKGROUND

Liver fluke are helminth parasites that cause a major economic loss in the livestock industry primarily by infection with *Fasciola hepatica* or its tropical counterpart *Fasciola gigantica*. Since all known drugs active against *F. hepatica* are also active against *F. gigantica*, the discussion that follows will refer to them collectively as *Fasciola* spp.

The primary impact of *Fasciola* spp infection is on farmed ruminants, however, they are not selective regarding the final host and successfully infect a wide range of mammals, including humans. Among the farmed ruminants, *Fasciola* spp may cause annual economic losses of several billions of dollars world-wide. McVeigh et al., Trends in Parasitology, March, 2018, Vol. 34, No. 3 184-196.

The liver fluke has a complex life cycle. In its final host *Fasciola* spp can be categorized into three stages, early immature, immature, and mature (commonly termed the adult stage). In sheep the early immature form occurs with flukes of 1-3 weeks of age, the immature form occurs with flukes of 4-7 weeks of age, and the mature form occurs with flukes of 8 weeks and older. In cattle the early immature form occurs with flukes of 1-5 weeks of age, the immature form occurs with flukes of 6-9 weeks of age, and the mature form occurs with flukes of 10 weeks and older.

Some anthelmintic drugs are only effective against the adult parasites often requiring more frequent applications, while many have now lost their advantage in the chemoprophylaxis of fasciolosis due to the development of drug resistance.

In Australia, drug resistance in *F. hepatica* to several anthelmintic drugs has been demonstrated in the field and laboratory ((1990) Drug resistance in *Fasciola hepatica*. In: Boray J C, Martin P J, Roush R T (eds) Resistance of parasites to antiparasitic drugs MSD AGVET, Rahway, N.J., pp 51-60 and D. Boray J. C., De Bono Drug resistance in *Fasciola hepatica*, Outteridge P M, Richards R B (eds) Australian advances in veterinary science (1989). The Australian Veterinary Association, pp 166-169). It has been shown that long and regular use of salicylanilide compounds, particular rafoxanide and closantel in sheep has selected for resistant strains of *F. hepatica* in endemic areas of New South Wales. These strains have been shown to retain their resistant status in cattle and through several passages in sheep. Of seventeen isolates from different geographical regions, ten (58.8%) showed resistance to rafoxanide at recommended doses in *F. hepatica* and side resistance to closantel was evident. Resistance to drugs was particularly manifested by immature *F. hepatica* but rarely by the adult fluke. Treatments of liver fluke infections with improved efficacy are desired.

DETAILED DESCRIPTION

The present invention provides for a method of treating liver fluke infections in a mammal in need of such treatment comprising administering an effective amount of diamphenethide in combination with an effective amount of clorsulon. Synergistic combinations of diamphenethide and clorsulon will have advantages regarding the efficacy against susceptible and resistant *Fasciola* spp.

Diamphenethide is also known by the chemical name N-[4-[2-[2-(4-acetamidophenoxy)ethoxy]ethoxy]phenyl]acetamide. The preparation of diamphenethide is well known in the art. For example, U.S. Pat. No. 3,896,235. Diamphenethide has been used against liver flukes and is rapidly metabolized by deacylation to a compound known as DAMD. Diamphenethide has been found to be highly effective against early immature flukes up to 6 weeks of age but shows progressively lower activity against flukes as they develop to maturity. Fairweather et al., The Veterinary Journal 1999, 158, 81-112. Diamphenethide was marketed under the tradename Coriban® for treatment of liver fluke infection in sheep and was removed from the market in the early 1980s. The recommended oral dose for sheep was 80-120 mg/kg.

Clorsulon is also known by the chemical name 4-amino-6-(1,2,2-trichloroethenyl)benzene-1,3-disulfonamide. The preparation of clorsulon is well known in the art. For example, U.S. Pat. No. 4,064,239. Clorsulon is thought to be effective against mature flukes and is more effective in cattle than in sheep. Clorsulon in combination with ivermectin is marketed under the tradename Ivomec Plus® and others, for treatment of mature liver flukes in cattle.

The term "liver fluke infection" refers to infection with *Fasciola hepatica* or *Fasciola gigantica*. Unless otherwise indicated the term includes infection by flukes at any stage of maturity and mixtures of stages of maturity.

The term "mammal" refers to warm-blooded vertebrate animals having hair or fur and secrete milk by the females for the nourishment of the young and includes humans. Particular mammals are ruminants, for example cattle, sheep, goats, bison, African buffalo, water buffalo, antelopes, deer, moose, elks, and giraffes. Also, included in the term mammal are the so-called pseudo-ruminants, for example, llamas and alpacas. Also, included in the term mammal are horses and donkies. More particularly, mammals are understood to be sheep, goats, bison, African buffalo, water buffalo, and cattle. Even more particularly, mammals are sheep and cattle.

The skilled clinician can readily determine a mammal in need of the present treatment. For example, symptoms include fever, malaise, abdominal pain, eosinophilia, enlarged liver, and abnormal liver tests. Also, infection can be detected by antibody testing, including ELISA testing, in particular of the blood and milk. The infection can also be diagnosed by examining fecal specimens, including by ELISA testing. Moreover, modeling based on season, rainfall, temperature, and other local conditions can be used to predict times when liver fluke infection is more likely.

The term "in combination with" as well as "combination" and "synergistic combination" as used herein are taken to mean that diamphenethide is administered prior to, during, or after the administration of clorsulon. That is, in the present combination diamphenethide and clorsulon are administered either sequentially or simultaneously to the mammal. Typically, sequentially administration means administration of either diamphenethide or clorsulon with three days of administration of the other. More typically, the diamphenethide and clorsulon are administered within a day of each other and even more typically on the same day. Sequential administration also means administration of either diamphenethide or clorsulon within an hour, or even minutes, of administration of the other. As a matter of convenience, the diamphenethide and clorsulon are administered simultaneously.

An effective amount of diamphenethide in combination with an effective amount of clorsulon is administered to the mammal orally or parenterally. In one embodiment, an effective amount of diamphenethide in combination with an effective amount of clorsulon is administered orally to the mammal. In one embodiment, an effective amount of diamphenethide in combination with an effective amount of clorsulon is administered parenterally to the mammal.

Oral administration can include adjuvants conventionally used in the art of formulation and may therefore be processed in a known manner to give, for example, solutions, emulsions, soluble powders, powder mixtures, granules or microencapsulation in polymeric substances. Such formulations, preparations or compositions containing diamphenethide and clorsulon, either separately or together, optionally include a solid or liquid adjuvant, and are produced in a manner well-known in the art, for example by intimately mixing and/or grinding the active ingredients with the adjuvants, for example with solvents, solid carriers, etc. Oral administration can also be accomplished by drench, gavage, tablet, capsule, or in feed.

The terms "effective amount of diamphenethide" and "effective amount of clorsulon" are taken to mean the amounts of diamphenethide and clorsulon necessary to either eliminate, nearly eliminate, slow, or arrest the progression of liver fluke infection when administered in the present combination.

In certain embodiments, the effective amount of diamphenethide in the present combination is 20-120 mg/kg (e.g., 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, or 120 mg/kg), and the effective amount of clorsulon in the present combination is 1-10 mg/kg (e.g, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg). In certain embodiments, the effective amount of diamphenethide in the present combination is 20-80 mg/kg (e.g., 20 mg/kg, 30 mg/kg, 40 mg/kg, 50 mg/kg, 60 mg/kg, 70 mg/kg, or 80 mg/kg), and the effective amount of clorsulon in the present combination is 1-10 mg/kg (e.g, 1.5 mg/kg, 3.5 mg/kg, 5 mg/kg, 7 mg/kg, or 10 mg/kg). In certain embodiments, the effective amount of diamphenethide in the present combination is 30-80 mg/kg, 40-80 mg/kg, 50-80 mg/kg, 60-80 mg/kg, or 70-80 mg/kg. In certain embodiments, the effective amount of clorsulon in the present combination is 1.5-10 mg/kg, 3-10 mg/kg, 5-10 mg/kg, or 7-10 mg/kg. In certain embodiments, the effective amount of diamphenethide in the present combination is 30-60 mg/kg, 40-60 mg/kg, or 40-50 mg/kg. In certain embodiments, the effective amount of clorsulon in the present combination is 3-10 mg/kg, 5-10 mg/kg, 6-10 mg/kg, or 7-10 mg/kg.

In certain embodiments, for treatment of sheep the effective amount of diamphenethide in the present combination is 20-80 mg/kg and the effective amount of clorsulon in the present combination is 3.5-10 mg/kg. In certain embodiments, for treatment of sheep the effective amount of diamphenethide in the present combination is 20-60 mg/kg and the effective amount of clorsulon in the present combination is 5-10 mg/kg. In certain embodiments, for treatment of sheep the effective amount of diamphenethide in the present combination is 35 mg/kg and the effective amount of clorsulon in the present combination is 5 mg/kg.

In certain embodiments, for treatment of cattle the effective amount of diamphenethide in the present combination is 40-120 mg/kg and the effective amount of clorsulon in the present combination is 3.5-10 mg/kg. In certain embodiments, for treatment of cattle the effective amount of diamphenethide in the present combination is 40-80 mg/kg and the effective amount of clorsulon in the present combination is 5-10 mg/kg. In certain embodiments, for treatment of cattle the effective amount of diamphenethide in the present combination is 70 mg/kg and the effective amount of clorsulon in the present combination is 10 mg/kg.

The present invention provides for a method of treating liver fluke infections in a mammal in need of such treatment comprising administering an effective amount of diamphenethide in combination with an effective amount of clorsulon. In another embodiment, the mammal is a ruminant. In another embodiment, the mammal is selected from the group consisting of sheep and cattle. In another embodiment, the mammal is sheep. In another embodiment, the mammal is cattle. In another embodiment, the effective amount of diamphenethide in the combination is 20-80 mg/kg (e.g., 20 mg/kg, 30 mg/kg, 40 mg/kg, 50 mg/kg, 60 mg/kg, 70 mg/kg, or 80 mg/kg). In another embodiment, the effective dose of clorsulon in the combination is 1-10 mg/kg (e.g, 1.5 mg/kg, 3.5 mg/kg, 5 mg/kg, 7 mg/kg, or 10 mg/kg). In certain embodiments, the effective amount of diamphenethide is 30-80 mg/kg, 40-80 mg/kg, 50-80 mg/kg, 60-80 mg/kg, or 70-80 mg/kg. In certain embodiments, the effective amount of clorsulon is 1.5-10 mg/kg, 3-10 mg/kg, 5-10 mg/kg, or 7-10 mg/kg.

The present invention also relates to the use of a combination of diamphenethide and clorsulon in the manufacture of a medicament for the treatment of liver fluke infections. In another embodiment, the use of diamphenethide in the combination is 20-80 mg/kg (e.g., 20 mg/kg, 30 mg/kg, 40 mg/kg, 50 mg/kg, 60 mg/kg, 70 mg/kg, or 80 mg/kg). In another embodiment, the use of clorsulon in the combination is 1-10 mg/kg (e.g, 1.5 mg/kg, 3.5 mg/kg, 5 mg/kg, 7 mg/kg, or 10 mg/kg). In certain embodiments, the effective amount of diamphenethide is 30-80 mg/kg, 40-80 mg/kg, 50-80 mg/kg, 60-80 mg/kg, or 70-80 mg/kg. In certain embodiments, the effective amount of clorsulon is 1.5-10 mg/kg, 3-10 mg/kg, 5-10 mg/kg, or 7-10 mg/kg.

Various aspects of the disclosure are set out in the following numbered clauses:

Clause 1. A method of treating liver fluke infections in a mammal in need of such treatment comprising administering an effective amount of diamphenethide in combination with an effective amount of clorsulon.

Clause 2. The method of clause 1 wherein the mammal is selected from the group consisting of sheep and cattle.

Clause 3. The method of clause 1 wherein the mammal is sheep.

Clause 4. The method of clause 1 wherein the mammal is cattle.

Clause 5. The method of any one of clauses 1-4, wherein the effective amount of diamphenethide is 20-80 mg/kg, 30-80 mg/kg, 40-80 mg/kg, 50-80 mg/kg, 60-80 mg/kg, or 70-80 mg/kg.

Clause 6. The method of any one of clauses 1-5, wherein the effective amount of diamphenethide is 20 mg/kg, 30 mg/kg, 40 mg/kg, 50 mg/kg, 60 mg/kg, 70 mg/kg, or 80 mg/kg.

Clause 7. The method of any one of clauses 1-6, wherein the effective amount of clorsulon is 1-10 mg/kg, 1.5-10 mg/kg, 3-10 mg/kg, 5-10 mg/kg, or 7-10 mg/kg.

Clause 8. The method of any one of clauses 1-7, wherein the effective amount of clorsulon is 1.5 mg/kg, 3.5 mg/kg, 5 mg/kg, 7 mg/kg, or 10 mg/kg.

Clause 9. The method of any one of clauses 1-8, wherein the liver fluke is *Fasciola hepatica*.

Clause 10. The method of any one of clauses 1-8, wherein the liver fluke is *Fasciola gigantica*.

Clause 11. The method of any one of clauses 1-10, wherein the liver fluke infection is an early immature stage liver fluke infection.

Clause 12. The method of any one of clauses 1-10, wherein the liver fluke infection is an immature stage liver fluke infection.

Clause 13. The method of any one of clauses 1-10, wherein the liver fluke infection is a mature stage liver fluke infection.

Clause 14. The use of a combination of an effective amount of diamphenethide and an effective amount of clorsulon for the treatment of liver fluke infections in a mammal in need of such treatment.

Clause 15. The use of clause 14 wherein the mammal is selected from the group consisting of sheep and cattle.

Clause 16. The use of clause 14 wherein the mammal is sheep.

Clause 17. The use of clause 14 wherein the mammal is cattle.

Clause 18. The use of any one of clauses 14-17, wherein the effective amount of diamphenethide is 20-80 mg/kg, 30-80 mg/kg, 40-80 mg/kg, 50-80 mg/kg, 60-80 mg/kg, or 70-80 mg/kg.

Clause 19. The use of any one of clauses 14-18, wherein the effective amount of diamphenethide is 20 mg/kg, 30 mg/kg, 40 mg/kg, 50 mg/kg, 60 mg/kg, 70 mg/kg, or 80 mg/kg.

Clause 20. The use of any one of clauses 14-19, wherein the effective amount of clorsulon is 1-10 mg/kg, 1.5-10 mg/kg, 3-10 mg/kg, 5-10 mg/kg, or 7-10 mg/kg.

Clause 21. The use of any one of clauses 14-20, wherein the effective amount of clorsulon is 1.5 mg/kg, 3.5 mg/kg, 5 mg/kg, 7 mg/kg, or 10 mg/kg.

Clause 22. The use of any one of clauses 14-21, wherein the liver fluke is *Fasciola hepatica*.

Clause 23. The use of any one of clauses 14-21, wherein the liver fluke is *Fasciola gigantica*.

Clause 24. The use of any one of clauses 14-23, wherein the liver fluke infection is an early immature stage liver fluke infection.

Clause 25. The use of any one of clauses 14-23, wherein the liver fluke infection is an immature stage liver fluke infection.

Clause 26. The use of any one of clauses 14-23, wherein the liver fluke infection is a mature stage liver fluke infection.

Clause 27. The use of a combination of an effective amount of diamphenethide and an effective amount of clorsulon in the manufacture of a medicament for the treatment of liver fluke infections in a mammal in need of such treatment.

Clause 28. The use of clause 27 wherein the mammal is selected from the group consisting of sheep and cattle.

Clause 29. The use of clause 27 wherein the mammal is sheep.

Clause 30. The use of clause 27 wherein the mammal is cattle.

Clause 31. The use of any one of clauses 27-30, wherein the effective amount of diamphenethide is 20-80 mg/kg, 30-80 mg/kg, 40-80 mg/kg, 50-80 mg/kg, 60-80 mg/kg, or 70-80 mg/kg.

Clause 32. The use of any one of clauses 27-31, wherein the effective amount of diamphenethide is 20 mg/kg, 30 mg/kg, 40 mg/kg, 50 mg/kg, 60 mg/kg, 70 mg/kg, or 80 mg/kg.

Clause 33. The use of any one of clauses 27-32, wherein the effective amount of clorsulon is 1-10 mg/kg, 1.5-10 mg/kg, 3-10 mg/kg, 5-10 mg/kg, or 7-10 mg/kg.

Clause 34. The use of any one of clauses 27-33, wherein the effective amount of clorsulon is 1.5 mg/kg, 3.5 mg/kg, 5 mg/kg, 7 mg/kg, or 10 mg/kg.

Clause 35. The use of any one of clauses 27-34, wherein the liver fluke is *Fasciola hepatica*.

Clause 36. The use of any one of clauses 27-34, wherein the liver fluke is *Fasciola gigantica*.

Clause 37. The use of any one of clauses 27-36, wherein the liver fluke infection is an early immature stage liver fluke infection.

Clause 38. The use of any one of clauses 27-36, wherein the liver fluke infection is an immature stage liver fluke infection.

Clause 39. The use of any one of clauses 27-36, wherein the liver fluke infection is a mature stage liver fluke infection.

Clause 40. A synergistic combination of diamphenethide and clorsulon for the treatment of liver fluke infections in a mammal in need of such treatment.

Clause 41. The combination of clause 40 wherein the mammal is selected from the group consisting of sheep and cattle.

Clause 42. The combination of clause 40 wherein the mammal is sheep.

Clause 43. The combination of clause 40 wherein the mammal is cattle.

Clause 44. The combination of any one of clauses 40-43, comprising 20-80 mg/kg, 30-80 mg/kg, 40-80 mg/kg, 50-80 mg/kg, 60-80 mg/kg, or 70-80 mg/kg of diamphenethide.

Clause 45. The combination of any one of clauses 40-44, comprising 20 mg/kg, 30 mg/kg, 40 mg/kg, 50 mg/kg, 60 mg/kg, 70 mg/kg, or 80 mg/kg of diamphenethide.

Clause 46. The combination of any one of clauses 40-45, comprising 1-10 mg/kg, 1.5-10 mg/kg, 3-10 mg/kg, 5-10 mg/kg, or 7-10 mg/kg of clorsulon.

Clause 47. The combination of any one of clauses 40-46, comprising 1.5 mg/kg, 3.5 mg/kg, 5 mg/kg, 7 mg/kg, or 10 mg/kg of clorsulon.

Clause 48. The combination of any one of clauses 40-47, wherein the liver fluke is *Fasciola hepatica*.

Clause 49. The combination of any one of clauses 40-47, wherein the liver fluke is *Fasciola gigantica*.

Clause 50. The combination of any one of clauses 40-49, wherein the liver fluke infection is an early immature stage liver fluke infection.

Clause 51. The combination of any one of clauses 40-49, wherein the liver fluke infection is an immature stage liver fluke infection.

Clause 52. The combination of any one of clauses 40-49, wherein the liver fluke infection is a mature stage liver fluke infection.

Clause 53. The method of any one of clauses 1-13, the use of any one of clauses 14-39, or the combination of any one of clauses 40-52, wherein the diamphenethide and the clorsulon are administered sequentially.

Clause 54. The method of any one of clauses 1-13, the use of any one of clauses 14-39, or the combination of any one of clauses 40-52, wherein the diamphenethide and the clorsulon are administered simultaneously.

Clause 55. The method of any one of clauses 1-4, wherein, the effective amount of diamphenethide is 30-60 mg/kg, 40-60 mg/kg, or 40-50 mg/kg.

Clause 56. The method of clause 55, wherein the effective amount of diamphenethide is 30 mg/kg, 40 mg/kg, 50 mg/kg, or 60 mg/kg.

Clause 57. The method of clause 55 or clause 56, wherein the effective amount of clorsulon is 3-10 mg/kg, 5-10 mg/kg, 6-10 mg/kg, or 7-10 mg/kg.

Clause 58. The method of any one of clauses 55-57, wherein the effective amount of clorsulon is 3 mg/kg, 4 mg/kg, 5 mg/kg, 6 mg/kg, 7 mg/kg, 8 mg/kg, 9 mg/kg, or 10 mg/kg.

Clause 59. The method of clause 3, wherein the effective amount of diamphenethide is 20-60 mg/kg and the effective amount of clorsulon is 5-10 mg/kg.

Clause 60. The method of clause 4, wherein the effective amount of diamphenethide is 40-80 mg/kg and the effective amount of clorsulon is 5-10 mg/kg.

Clause 61. The method of any one of clauses 55-60, wherein the liver fluke is *Fasciola hepatica*.

Clause 62. The method of any one of clauses 55-60, wherein the liver fluke is *Fasciola gigantica*.

Clause 63. The method of any one of clauses 55-60, wherein the liver fluke infection is an early immature stage liver fluke infection.

Clause 64. The method of any one of clauses 55-60, wherein the liver fluke infection is an immature stage liver fluke infection.

Clause 65. The method of any one of clauses 55-60, wherein the liver fluke infection is a mature stage liver fluke infection.

Clause 66. The use of any one of clauses 14-17, wherein, the effective amount of diamphenethide is 30-60 mg/kg, 40-60 mg/kg, or 40-50 mg/kg.

Clause 67. The use of clause 66, wherein the effective amount of diamphenethide is 30 mg/kg, 40 mg/kg, 50 mg/kg, or 60 mg/kg.

Clause 68. The use of clause 66 or clause 67, wherein the effective amount of clorsulon is 3-10 mg/kg, 5-10 mg/kg, 6-10 mg/kg, or 7-10 mg/kg.

Clause 69. The use of any one of clauses 66-68, wherein the effective amount of clorsulon is 3 mg/kg, 4 mg/kg, 5 mg/kg, 6 mg/kg, 7 mg/kg, 8 mg/kg, 9 mg/kg, or 10 mg/kg.

Clause 70. The use of clause 16, wherein the effective amount of diamphenethide is 20-60 mg/kg and the effective amount of clorsulon is 5-10 mg/kg.

Clause 71. The use of clause 17, wherein the effective amount of diamphenethide is 40-80 mg/kg and the effective amount of clorsulon is 5-10 mg/kg.

Clause 72. The use of any one of clauses 66-71, wherein the liver fluke is *Fasciola hepatica*.

Clause 73. The use of any one of clauses 66-71, wherein the liver fluke is *Fasciola gigantica*.

Clause 74. The use of any one of clauses 66-71, wherein the liver fluke infection is an early immature stage liver fluke infection.

Clause 75. The use of any one of clauses 66-71, wherein the liver fluke infection is an immature stage liver fluke infection.

Clause 76. The use of any one of clauses 66-71, wherein the liver fluke infection is a mature stage liver fluke infection.

Clause 77. The use of any one of clauses 27-30, wherein, the effective amount of diamphenethide is 30-60 mg/kg, 40-60 mg/kg, or 40-50 mg/kg.

Clause 78. The use of clause 77, wherein the effective amount of diamphenethide is 30 mg/kg, 40 mg/kg, 50 mg/kg, or 60 mg/kg.

Clause 79. The use of clause 77 or clause 78, wherein the effective amount of clorsulon is 3-10 mg/kg, 5-10 mg/kg, 6-10 mg/kg, or 7-10 mg/kg.

Clause 80. The use of any one of clauses 77-79, wherein the effective amount of clorsulon is 3 mg/kg, 4 mg/kg, 5 mg/kg, 6 mg/kg, 7 mg/kg, 8 mg/kg, 9 mg/kg, or 10 mg/kg.

Clause 81. The use of clause 29, wherein the effective amount of diamphenethide is 20-60 mg/kg and the effective amount of clorsulon is 5-10 mg/kg.

Clause 82. The use of clause 30, wherein the effective amount of diamphenethide is 40-80 mg/kg and the effective amount of clorsulon is 5-10 mg/kg.

Clause 83. The use of any one of clauses 77-82, wherein the liver fluke is *Fasciola hepatica*.

Clause 84. The use of any one of clauses 77-82, wherein the liver fluke is *Fasciola gigantica*.

Clause 85. The use of any one of clauses 77-82, wherein the liver fluke infection is an early immature stage liver fluke infection.

Clause 86. The use of any one of clauses 77-82, wherein the liver fluke infection is an immature stage liver fluke infection.

Clause 87. The use of any one of clauses 77-82, wherein the liver fluke infection is a mature stage liver fluke infection.

Clause 88. The combination of any one of clauses 40-43, wherein the effective amount of diamphenethide is 30-60 mg/kg, 40-60 mg/kg, or 40-50 mg/kg.

Clause 89. The combination of clause 88, wherein the effective amount of diamphenethide is 30 mg/kg, 40 mg/kg, 50 mg/kg, or 60 mg/kg.

Clause 90. The combination of clause 88 or clause 89, wherein the effective amount of clorsulon is 3-10 mg/kg, 5-10 mg/kg, 6-10 mg/kg, or 7-10 mg/kg.

Clause 91. The combination of any one of clauses 88-90, wherein the effective amount of clorsulon is 3 mg/kg, 4, mg/kg, 5 mg/kg, 6 mg/kg, 7 mg/kg, 8 mg/kg, 9 mg/kg, or 10 mg/kg.

Clause 92. The combination of clause 42, wherein the effective amount of diamphenethide is 20-60 mg/kg (e.g., 35 mg/kg) and the effective amount of clorsulon is 5-10 mg/kg (e.g., 5 mg/kg).

Clause 93. The combination of clause 43, wherein the effective amount of diamphenethide is 40-80 mg/kg (e.g., 70 mg/kg) and the effective amount of clorsulon is 5-10 mg/kg (e.g., 10 mg/kg).

Clause 94. The combination of any one of clauses 88-93, wherein the liver fluke is *Fasciola hepatica*.

Clause 95. The combination of any one of clauses 88-93, wherein the liver fluke is *Fasciola gigantica*.

Clause 96. The combination of any one of clauses 88-93, wherein the liver fluke infection is an early immature stage liver fluke infection.

Clause 97. The combination of any one of clauses 88-93, wherein the liver fluke infection is an immature stage liver fluke infection.

Clause 98. The combination of any one of clauses 88-93, wherein the liver fluke infection is a mature stage liver fluke infection.

Clause 99. The method of any one of clauses 55-60, the use of any one of clauses 66-71 or 77-82, or the combination of any one of clauses 88-93, wherein the diamphenethide and the clorsulon are administered sequentially.

Clause 100. The method of any one of clauses 55-60, the use of any one of clauses 14-39, or the combination of any one of clauses 88-93, wherein the diamphenethide and the clorsulon are administered simultaneously.

Clause 101. The method of clause 1, the use of clause 14 or clause 27, or the combination of clause 40, wherein the effective amount of diamphenethide is 20 mg/kg or greater, 30 mg/kg or greater, 40 mg/kg or greater, 50 mg/kg or greater, 60 mg/kg or greater, 70 mg/kg or greater, 80 mg/kg or greater, 90 mg/kg or greater, 100 mg/kg or greater, 110 mg/kg or greater, or 120 mg/kg or greater.

Clause 102. The method of clause 1, the use of clause 14 or clause 27, or the combination of clause 40, wherein the effective amount of diamphenethide is 120 mg/kg or less, 110 mg/kg or less, 90 mg/kg or less, 80 mg/kg or less, 70 mg/kg or less, 60 mg/kg or less, 50 mg/kg or less, 40 mg/kg or less, 30 mg/kg or less, 20 mg/kg or less.

Clause 103. The method of clauses 1, 101, or 102, the use of clauses 14, 27, 101, or 102, or the combination of clauses 40, 101, or 102, wherein the effective amount of clorsulon is 1 mg/kg or greater, 1.5 mg/kg or greater, 2 mg/kg or greater, 2.5 mg/kg or greater, 3 mg/kg or greater, 3.5 mg/kg or greater, 4 mg/kg or greater, 4.5 mg/kg or greater, 5 mg/kg or greater, 5.5 mg/kg or greater, 6 mg/kg or greater, 6.5 mg/kg or greater, 7 mg/kg or greater, 7.5 mg/kg or greater, 8 mg/kg or greater, 8.5 mg/kg or greater, 9 mg/kg or greater, 9.5 mg/kg or greater, or 10 mg/kg or greater.

Clause 104. The method of clauses 1, 101, or 102, the use of clauses 14, 27, 101, or 102, or the combination of clauses 40, 101, or 102, wherein the effective amount of clorsulon is 10 mg/kg or less, 9.5 mg/kg or less, 9 mg/kg or less, 8.5 mg/kg or less, 8 mg/kg or less, 7.5 mg/kg or less, 7 mg/kg or less, 6.5 mg/kg or less, 6 mg/kg or less, 5.5 mg/kg or less, 5 mg/kg or less, 4.5 mg/kg or less, 4 mg/kg or less, 3.5 mg/kg or less, 3 mg/kg or less, 2.5 mg/kg or less, 2 mg/kg or less, 1.5 mg/kg or less, or 1 mg/kg or less.

Clause 105. The method of clause 1, the use of clause 14 or clause 27, or the combination of clause 40, wherein the effective amount of diamphenethide is 20-80 mg/kg, and the effective amount of clorsulon is 3.5-10 mg/kg.

Clause 106. The method of any one of clauses 101-105, the use of any one of clauses 101-105, or the combination of any one of clauses 101-105, wherein the mammal is sheep.

Clause 107. The method of any one of clauses 101-105, the use of any one of clauses 101-105, or the combination of any one of clauses 101-105, wherein the mammal is cattle.

Clause 108. The method, use, or combination of clause 106, wherein the effective amount of diamphenethide is 35 mg/kg and the effective amount of clorsulon is 5 mg/kg.

Clause 109. The method, use, or combination of clause 107, wherein the effective amount of diamphenethide is 70 mg/kg and the effective amount of clorsulon is 10 mg/kg.

Clause 110. The method of any one of clauses 101-109, the use of any one of clauses 101-109, or the combination of any one of clauses 101-109, wherein the liver fluke is *Fasciola hepatica*.

Clause 111. The method of any one of clauses 101-109, the use of any one of clauses 101-109, or the combination of any one of clauses 101-109, wherein the liver fluke is *Fasciola gigantica*.

Clause 112. The method of any one of clauses 101-111, the use of any one of clauses 101-111, or the combination of any one of clauses 101-111, wherein the liver fluke infection is an early immature stage liver fluke infection.

Clause 113. The method of any one of clauses 101-111, the use of any one of clauses 101-111, or the combination of any one of clauses 101-111, wherein the liver fluke infection is an immature stage liver fluke infection.

Clause 114. The method of any one of clauses 101-111, the use of any one of clauses 101-111, or the combination of any one of clauses 101-111, wherein the liver fluke infection is a mature stage liver fluke infection.

Clause 115. The method, use or combination of any preceding clause, wherein the method, use or combination exhibits an efficacy of 80% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater for the treatment of liver fluke infection.

Clause 116. The method, use, or combination of any preceding clause, wherein the method, use or combination exhibits an efficacy of 85-99%.

Clause 117. The method, use, or combination of any preceding clause, wherein the method, use or combination exhibits an efficacy of 85-96%.

Clause 118. The method, use, or combination of any one of clauses 115-117, wherein assessment of efficacy is based on the number of live fluke removed from the mammal liver compared to an untreated control.

Clause 119. The method, use or combination of clause 118, wherein assessment occurs on the liver with gall bladder and common bile duct intact recovered 40-80 days after treatment (e.g., 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 days after treatment).

The following examples illustrate the improved efficacy of the combination of diamphenethide and clorsulon in sheep and cattle. It is understood that the examples are set forth by way of illustration and not limitation.

In the following examples, all animals were confirmed free of infection with *F. hepatica* and found clinically healthy by a veterinarian prior to enrollment in the study. Doses were administered orally from suitably sized disposable syringes.

The fluke counts and body weights were log-transformed (after adding a constant of 1 to the fluke counts only) and the distribution of the transformed data checked to see if they satisfied the assumption of normal distribution. Differences between treatment groups were analyzed by analysis of variance methods (ANOVA), as the assumptions of normal distribution were satisfied for log-transformed fluke count and log-transformed bodyweight, as well as for (untransformed) fluke measurements.

Arithmetic means (Amean), geometric means (Gmean), median and ranges were summarized for fluke counts, fluke measurements and bodyweight. A constant of one was applied for calculation of geometric means of fluke counts.

The percentage efficacy for each treated group was calculated as follows:

$$\% \text{ Efficacy} = 100 \times (FC_C - FC_T)/FC_C$$

where $FC_C$ is the arithmetic mean fluke count of the control group and $FC_T$ is the arithmetic mean fluke count of the treated group. The formula was also applied using mean geometric fluke counts; these were calculated using log transformed data with 1 added as a constant to each fluke count and then subtracted following transformation.

A synergistic effect was concluded if:

$$(1 - \text{Efficacy}_{D+C}) < (1 - \text{Efficacy}_D) \times (1 - \text{Efficacy}_C)$$

where D=Diamphenethide and C=Clorsulon and efficacies are measured as absolute numbers (not in %).

Note that expected synergy is defined as:

$$1-\text{Efficacy(expected without synergy)}=(1-\text{Efficacy}_D)\times(1-\text{Efficacy}_C).$$

Example 1

Typical formulations of diamphenethide and clorsulon are provided in Example 1. Suspension of diamphenethide was prepared as follows: place propylene glycol into a glass beaker. Add both parabenes and stir until dissolved. Add Polysorbate 80, antifoam emulsion and water and stir until homogeneity is reached. Add Avicel RC591 very slowly while stirring. Afterward homogenize with an Ultra-Turrax® for several minutes, add diamphenethide slowly while stirring and homogenize with an Ultra-Turrax® again for at least 10 minutes to give a suspension having the composition below:

1. Diamphenethide 15% (w/v)
2. Propylene glycol 5% (w/v)
3. Methylparaben 0.11% (w/v)
4. Propylparaben 0.04% (w/v)
5. Polysorbate 80 0.5% (w/v)
6. Avicel RC 591 1.2% (w/v)
7. Antifoam emulsion 0.6% (w/v)
8. Demineralised water ad 100.

Suspension of clorsulon was prepared as follows: Heat water, add both parabenes and stir until they are dissolved. Cool to ambient temperature and add SDS and antifoam emulsion and stir until homogeneity is reached. Add Avicel RC591 very slowly while stirring. Afterward homogenize with an Ultra-Turrax® for several minutes Add clorsulon slowly while stirring and homogenize with an Ultra-Turrax® again for at least 10 minutes to give a suspension having the composition below:

1. Clorsulon 3.5% (w/v)
2. Methylparaben 0.11% (w/v)
3. Propylparaben 0.04% (w/v)
4. SDS (sodium lauryl sulfate) 0.1% (w/v)
5. Avicel RC 591 1.2% (w/v)
6. Antifoam emulsion 0.5% (w/v)
7. Demineralised water ad 100.

Example 2

Evaluation of the Synergistic Effect of Diamphenetide Administered Concurrently with Clorsulon Against the Immature Stage of *Fasciola hepatica* Infections in Sheep This study was to assess the efficacy of diamphenethide (40 mg/kg) given concurrently with clorsulon (3.5 mg/kg), diamphenethide alone (40 mg/kg), and clorsulon alone (3.5 mg/kg) against *F. hepatica* in sheep with treatment on day 42. This was a controlled, blinded, randomized study using 3-4 month old Merino lambs.

On day 0, the sheep were experimentally infected with a target of 200 "Sunny Corner" (laboratory strain reference Fashep-66) *F. hepatica* metacercariae. The required number of metacercariae were prepared for infection in a water and 4% carboxymethylcellulose solution. Each infective dose was followed by water administered orally. Syringes were subsequently checked post-infection for retained metacercariae and it was determined that the sheep were administered between 93.5% and 100% (98.3% on average) of the target infective dose.

The sheep were randomized into treatment groups on the basis of day 41 body weight and allocated to groups as denoted in Table 2.1.

TABLE 2.1

| Group | Treatment | Dose (mg/kg) | n |
|---|---|---|---|
| 1 | Untreated | — | 5 |
| 2 | Diamphenethide | 40 | 5 |
| 3 | Clorsulon | 3.5 | 5 |
| 4 | Diamphenethide and Clorsulon | 40 and 3.5 | 5 |

Body weight was determined one day prior to treatments, which were measured by volume and rounded to the nearest 0.1 mL. On day 42, and before feeding, the individual animals were treated once only with the Treatment in Table 2.1. Once the animals had been treated they were returned to their pens and fed within one hour. Untreated control animals were also fed at this time.

The liver with gall bladder and common bile duct intact were recovered on day 91 from each animal and processed for *F. hepatica* counts. The assessment of efficacy was based on the number of live fluke removed from the liver.

An ANOVA model was used to compare fluke counts between treatment groups. The model was applied to the log-transformed counts. There was one fixed effect, treatment group.

All control sheep in Group 1 were positive for *F. hepatica* infection, with a geometric mean of 87.02. The percentage efficacy for treated sheep were compared to those of the sheep in the untreated control group as shown in Table 2.2 below.

TABLE 2.2

| Group | Treatment | Fluke Count[1] | % Efficacy[2] | Fluke Count[3] | % Efficacy[4] |
|---|---|---|---|---|---|
| 1 | Untreated Control | 90.2 | — | 87.0 | — |
| 2 | Diamphenethide | 57.6 | 36.1 | 50.9 | 41.5 |
| 3 | Clorsulon | 81.8 | 9.3 | 79.7 | 8.4 |
| 4 | Diamphenethide and Clorsulon | 18.2 | 79.8 | 11.3 | 87.0 |

[1]Arithmetic mean;
[2]Using Arithmetic mean;
[3]Geometric Mean;
[4]Using Geometric Mean Pair-wise comparisons demonstrated the concurrent treatment to have significantly lower fluke counts than the untreated and single formulation treated groups as shown in Table 2.3.

TABLE 2.3

| Group | 2 | 3 | 4 |
|---|---|---|---|
| 1 | 0.1947 | 0.8268 | <0.0001 |
| 2 |  | 0.2768 | 0.0013 |
| 3 |  |  | <0.0001 |
| 4 |  |  |  |

Expected and observed % Efficacy against *F. hepatica* for concurrent treatments is presented in Table 2.4.

TABLE 2.4

| | | Amean | | Gmean | |
|---|---|---|---|---|---|
| Group | Treatment | Expected | Observed | Expected | Observed |
| 4 | Diamphenethide + Clorsulon | 42.1 | 79.8 | 46.4 | 87.0 |

The observed efficacy of concurrent treatment of diamphenethide and clorsulon was higher than the expected additive effect demonstrating a synergistic effect.

Example 3

Evaluation of the Synergistic Effect of Diamphenethide Administered Concurrently with Clorsulon Against the Early Immature Stage of *Fasciola hepatica* Infections in Sheep This study was to assess the efficacy of diamphenethide (20 mg/kg) given concurrently with clorsulon (10 mg/kg), diamphenethide alone (20 mg/kg), and clorsulon alone (10 mg/kg) against *F. hepatica* in sheep with treatment on day 14. This was a controlled, blinded, randomized study using sheep.

On day 0, the sheep were experimentally infected with a target of 200 "Sunny Corner" (laboratory strain reference Fashep-66) *F. hepatica* metacercariae. The required number of metacercariae were prepared for infection in a water and 2% carboxymethylcellulose solution. Each infective dose was followed by water administered orally.

The sheep were randomized into treatment groups on the basis of day 13 body weight and allocated to groups as denoted in Table 3.1. Animals were treated on day 14 with a single dose as noted in Table 3.1.

TABLE 3.1

| Group | Treatment | Dose (mg/kg) | n |
|---|---|---|---|
| 1 | Untreated | — | 5 |
| 2 | Diamphenethide | 20 | 5 |
| 3 | Clorsulon | 10 | 5 |
| 4 | Diamphenethide and Clorsulon | 20 and 10 | 5 |

Body weight was determined one day prior to treatments, which were measured by volume and rounded to the nearest 0.1 mL. On day 14, and before feeding, the individual animals were treated once only with the Treatment in Table 3.1. Once the animals had been treated they were returned to their pens and fed. Untreated control animals were also fed at this time.

The liver with gall bladder and common bile duct intact were recovered on day 91 from each animal and processed for *F. hepatica* counts. The assessment of efficacy was based on the number of live fluke removed from the liver.

An ANOVA model was used to compare fluke counts between treatment groups. The model was applied to the log-transformed counts. There was one fixed effect, treatment group.

All control sheep in Group 1 were positive for *F. hepatica* infection, with a geometric mean of 137.3. The percentage efficacy for treated sheep were compared to those of the sheep in the untreated control group as shown in Table 3.2 below.

TABLE 3.2

| Group | Treatment | Fluke Count[1] | % Efficacy[2] | Fluke Count[3] | % Efficacy[4] |
|---|---|---|---|---|---|
| 1 | Untreated Control | 139.0 | — | 137.3 | — |
| 2 | Diamphenethide | 89.0 | 40.0 | 87.5 | 36.3 |
| 3 | Clorsulon | 99.8 | 28.2 | 90.6 | 34.0 |
| 4 | Diamphenethide and Clorsulon | 9.8 | 92.9 | 7.8 | 94.3 |

[1]Arithmetic mean;
[2]Using Arithmetic mean;
[3]Geometric Mean;
[4]Using Geometric Mean Pair-wise comparisons demonstrated the concurrent treatment to have significantly lower fluke counts than the untreated and single formulation treated groups and the single active treatments were not significantly different from each other, in regards to fluke count, as shown in Table 3.3.

TABLE 3.3

| Group | 2 | 3 | 4 |
|---|---|---|---|
| 1 | 0.1510 | 0.1831 | <0.0001 |
| 2 | | 0.9086 | <0.0001 |
| 3 | | | <0.0001 |

Expected and observed % Efficacy against *F. hepatica* for concurrent treatments is presented in Table 3.4.

TABLE 3.4

| | | Amean | | Gmean | |
|---|---|---|---|---|---|
| Group | Treatment | Expected | Observed | Expected | Observed |
| 4 | Diamphenethide + Clorsulon | 53.9 | 92.9 | 57.9 | 94.3 |

The observed efficacy of concurrent treatment of diamphenethide and clorsulon was higher than the expected additive effect demonstrating a synergistic effect.

Example 4

Evaluation of the Synergistic Effect of Diamphenethide Administered Concurrently with Clorsulon Against the Immature Stage of *Fasciola hepatica* Infections in Cattle This study was to assess the efficacy of diamphenethide (60 mg/kg) given concurrently with clorsulon (5 mg/kg), diamphenethide alone (60 mg/kg), and clorsulon alone (5 mg/kg) against *F. hepatica* in in cattle with treatment on day 49. This was a controlled, blinded, randomized study.

On day 0, the calves were experimentally infected with a single isolate of approximately 382 Sunny Corner (Fashep-66) isolate *F. hepatica* metacercariae. The required number of metacerceriae were made up in 2% carboxymethyl cellulose. Syringes were checked post-infection for retained metacerceriae. The infection was administered orally and each infective dose was followed by water administered orally. The cattle were randomized into treatment groups on the basis of day 48 body weight and allocated to groups as denoted in Table 4.1.

TABLE 4.1

| Group | Treatment | Dose (mg/kg) | n |
|---|---|---|---|
| 1 | Untreated | — | 5 |
| 2 | Diamphenethide | 60 | 5 |
| 3 | Clorsulon | 5 | 5 |
| 4 | Diamphenethide and Clorsulon | 60 and 5 | 5 |

Body weight was determined one day prior to treatment. All treatments were measured by volume and rounded to the nearest 0.1 mL. On day 49, and before feeding, the individual animals were treated once only with the treatment in Table 4.1. Once the animals had been treated they were returned to their pens and fed within one hour. Untreated control animals were also fed at this time.

The liver with gall bladder and bile ducts intact were recovered from each animal on day 91 or 92 and processed for *F. hepatica* counts. The assessment of efficacy was based on the number of live fluke removed from the liver.

The percentage efficacy for treated cattle were compared to those of the cattle in the untreated control group as shown in Table 4.2 below.

TABLE 4.2

| Group | Treatment | Fluke Count[1] | % Efficacy[2] | Fluke Count[3] | % Efficacy[4] |
|---|---|---|---|---|---|
| 1 | Untreated Control | 84.0 | — | 83.5 | — |
| 2 | Diamphenethide | 73.8 | 12.1 | 61.8 | 26.0 |
| 3 | Clorsulon | 72.6 | 13.6 | 70.7 | 15.3 |
| 4 | Diamphenethide and Clorsulon | 5.2 | 93.8 | 4.5 | 94.6 |

[1]Arithmetic mean;
[2]Using Arithmetic mean;
[3]Geometric Mean;
[4]Using Geometric Mean Pair-wise comparisons demonstrated the concurrent treatment to have significantly lower fluke counts than the untreated and single formulation treated groups and the single active treatments were not significantly different from each other, in regards to fluke count, as shown in Table 4.3.

TABLE 4.3

| Group | 2 | 3 | 4 |
|---|---|---|---|
| 1 | 0.3440 | 0.5979 | <0.0001 |
| 2 |  | 0.6679 | <0.0001 |
| 3 |  |  | <0.0001 |

Expected and observed % Efficacy against *F. hepatica* for concurrent treatments is presented in Table 4.4.

TABLE 4.4

| | | Amean | | Gmean | |
|---|---|---|---|---|---|
| Group | Treatment | Expected | Observed | Expected | Observed |
| 4 | Diamphenethide + Clorsulon | 24.1 | 93.8 | 37.2 | 94.6 |

The observed efficacy of concurrent treatment of diamphenethide and clorsulon was higher than the expected additive effect demonstrating a synergistic effect.

Example 5

Evaluation of the Synergistic Effect of Diamphenethide Administered Concurrently with Clorsulon Against the Early Immature Stage of *Fasciola hepatica* Infections in Cattle This study was to assess the efficacy of diamphenethide (40 mg/kg) given concurrently with clorsulon (7 mg/kg), diamphenethide alone (40 mg/kg), and clorsulon alone (7 mg/kg) against *F. hepatica* in in cattle with treatment on day 21. This was a controlled, blinded, randomized study.

On day 0, the calves were experimentally infected with a single isolate of approximately 350 Sunny Corner (Fashep-66) isolate *F. hepatica* metacercariae. The required number of metacerceriae were made up in 2% carboxymethyl cellulose. Syringes were checked post-infection for retained metacerceriae. The infection was administered orally and each infective dose was followed by water administered orally. The cattle were randomized into treatment groups on the basis of day 20 body weight and allocated to groups as denoted in Table 5.1.

TABLE 5.1

| Group | Treatment | Dose (mg/kg) | n |
|---|---|---|---|
| 1 | Untreated | — | 5 |
| 2 | Diamphenethide | 40 | 5 |
| 3 | Clorsulon | 7 | 5 |
| 4 | Diamphenethide and Clorsulon | 40 and 7 | 5 |

Body weight was determined one day prior to treatment. All treatments were measured by volume and rounded to the nearest 0.1 mL. On day 21, and before feeding, the individual animals were treated once only with the treatment in Table 4.1. Once the animals had been treated they were returned to their pens and fed within one hour. Untreated control animals were also fed at this time.

The liver with gall bladder and bile ducts intact were recovered from each animal on day 91 or 92 and processed for *F. hepatica* counts. The assessment of efficacy was based on the number of live fluke removed from the liver.

The percentage efficacy for treated cattle were compared to those of the cattle in the untreated control group as shown in Table 5.2 below.

TABLE 5.2

| Group | Treatment | Fluke Count[1] | % Efficacy[2] | Fluke Count[3] | % Efficacy[4] |
|---|---|---|---|---|---|
| 1 | Untreated Control | 78.2 | — | 73.2 | — |
| 2 | Diamphenethide | 54.2 | 30.7 | 53.1 | 27.5 |
| 3 | Clorsulon | 45.2 | 42.2 | 42.4 | 42.1 |
| 4 | Diamphenethide and Clorsulon | 3.8 | 95.1 | 2.5 | 96.6 |

[1]Arithmetic mean;
[2]Using Arithmetic mean;
[3]Geometric Mean;
[4]Using Geometric Mean Pair-wise comparisons demonstrated the concurrent treatment to have significantly lower fluke counts than the untreated and single formulation treated groups and the single active treatments were not significantly different from each other, in regards to fluke count, as shown in Table 5.3.

TABLE 5.3

| Group | 2 | 3 | 4 |
|---|---|---|---|
| 1 | 0.3875 | 0.1504 | <0.0001 |
| 2 |  | 0.5425 | <0.0001 |
| 3 |  |  | <0.0001 |

Expected and observed % Efficacy against *F. hepatica* for concurrent treatments is presented in Table 5.4.

TABLE 5.4

| Group | Treatment | Amean | | Gmean | |
|---|---|---|---|---|---|
| | | Expected | Observed | Expected | Observed |
| 4 | Diamphenethide + Clorsulon | 59.9 | 95.1 | 58.0 | 96.6 |

The observed efficacy of concurrent treatment of diamphenethide and clorsulon was higher than the expected additive effect demonstrating a synergistic effect.

What is claimed is:

1. A method of treating liver fluke infections in a mammal in need of such treatment comprising administering an effective amount of diamphenethide in combination with an effective amount of clorsulon,
   wherein the effective amount of diamphenethide is 20-80 mg/kg; and
   wherein the effective amount of clorsulon is 3-10 mg/kg.

2. The method of claim 1, wherein the mammal is selected from the group consisting of sheep and cattle.

3. The method of claim 1, wherein the mammal is sheep.

4. The method of claim 1, wherein the mammal is cattle.

5. The method of claim 1, wherein the effective amount of diamphenethide is 20 mg/kg, 30 mg/kg, 40 mg/kg, 50 mg/kg, 60 mg/kg, 70 mg/kg, or 80 mg/kg.

6. The method of claim 1, wherein the effective amount of clorsulon is 3.5 mg/kg, 5 mg/kg, 7 mg/kg, or 10 mg/kg.

7. The method of claim 1, wherein the liver fluke is *Fasciola hepatica*.

8. The method of claim 1, wherein the liver fluke is *Fasciola gigantica*.

* * * * *